United States Patent
Haulsee et al.

(10) Patent No.: US 8,476,192 B2
(45) Date of Patent: Jul. 2, 2013

(54) SEED TREATMENT PESTICIDAL COMPOSITIONS

(75) Inventors: Lear Michael Haulsee, Winston Salem, NC (US); Humberto B. Lopez, Livermore, CA (US)

(73) Assignee: Syngenta Crop Protection LLC, Greensboro, NC (US)

( * ) Notice: Subject to any disclaimer, the term of this patent is extended or adjusted under 35 U.S.C. 154(b) by 1341 days.

(21) Appl. No.: 10/598,083

(22) PCT Filed: Mar. 15, 2005

(86) PCT No.: PCT/EP2005/002754
§ 371 (c)(1),
(2), (4) Date: Aug. 17, 2006

(87) PCT Pub. No.: WO2005/089545
PCT Pub. Date: Sep. 29, 2005

(65) Prior Publication Data
US 2007/0196358 A1    Aug. 23, 2007

Related U.S. Application Data

(60) Provisional application No. 60/553,495, filed on Mar. 16, 2004.

(30) Foreign Application Priority Data

Jun. 2, 2004 (EP) .................................... 04012960

(51) Int. Cl.
*A01N 25/26* (2006.01)
*A01N 43/02* (2006.01)
*A01N 43/16* (2006.01)
*A61K 31/33* (2006.01)
*A61K 31/35* (2006.01)
*A61K 31/355* (2006.01)

(52) U.S. Cl.
USPC ........... 504/100; 514/183; 514/450; 514/456; 514/458

(58) Field of Classification Search
None
See application file for complete search history.

(56) References Cited

U.S. PATENT DOCUMENTS

2003/0050194 A1 * 3/2003 Hopkinson et al. ............ 504/363
2005/0215432 A1 * 9/2005 Schlatter et al. ............... 504/100

FOREIGN PATENT DOCUMENTS

| WO | 01-20986 A1 | 3/2001 |
| WO | 01-30147 A1 | 5/2001 |
| WO | 01-60159 A1 | 8/2001 |

OTHER PUBLICATIONS

S. J. Maude: "The effects of surfactant and water volume on the coverage of seed surface by a seed treatment formulation." ; BCPC Conf. Pests and Diseases, vol. 2, 2002, pp. 507-514, XP009034608, p. 50, paragraph 3 table 1; p. 511, paragraphs 3,4 figures 4,5; p. 513, paragraph 1.

* cited by examiner

*Primary Examiner* — Alton Pryor
(74) *Attorney, Agent, or Firm* — Brian McAlhaney

(57) ABSTRACT

An aqueous seed treatment insecticidal and/or nematicidal composition in the form of a suspension comprising (A) at least one insecticide and/or nematicide in an amount of at least 3 weight %, based on the total weight of the composition, and (B) at least two surface active compounds, wherein (i) at least one is an anionic phosphate type compound, and (ii) at least one is a non-ionic alkoxylated phenol. Such compositions demonstrate improved dust-off performance when applied to plant propagation material, such as seeds.

10 Claims, No Drawings

SEED TREATMENT PESTICIDAL COMPOSITIONS

This application is a 371 of International Application No, PCT/EP2005/002754 filed Mar. 15, 2005, which claims priority to U.S. 60/553,495 filed Mar. 16, 2004, and EP 04012960.3 filed Jun. 2, 2004, the contents of which are incorporated herein by reference.

The present invention relates to an aqueous seed treatment insecticidal and/or nematicidal composition and a slurry composition comprising the composition, which compositions are used in treating plant propagation material to protect it against attack by pests; to a pest resistant plant propagation material; to a method of protecting plant propagation material; to a method of controlling pests from crop plants; to use of certain surface active compounds for improving characteristics of the treated material; and to the use of the surface active compounds for improving compatibility between pesticidal compositions.

Treatment of plant propagation material with pesticidal compositions allows protection against soil-borne pests during a susceptible stage in plant's development. Further, systemic seed treatments may provide an alternative to the traditional foliar pesticide applications. However, following such treatment, the treated plant propagation material is handled and conveyed for packing and storage; this handling and conveying often results in the treated material brushing against each other to cause the chemicals that were bound to the material to become unbound. The release of the chemicals is often in the form of air-borne particles of, for example, pesticides and other materials from the treating composition that on drying the seed form solid particles. This can result in the treated material losing its pesticidal effectiveness and exposing workers in such treatment operations to health risks, through inhalation and sensitisation, for example, eye irritancy, of the air-borne particles. Further, treatment of plant propagation material is often carried out in a slurry composition containing a mixture of pesticidal compositions, which can result in incompatibility difficulties, i.e., resulting in flocculation and inhomogeneity, between the different pesticidal compositions. It has been noted that pesticidal compositions having a low pH are particularly difficult to formulate compatible slurries.

Accordingly, formulators are faced with the challenge of:
how to improve the adherence of such particles to the plant propagation material, and
how to provide compositions that satisfy compatibility requirements.

It has been found that a pesticidal composition comprising certain type of surface active compounds provides unexpected reduction in the air-borne particles (commonly referred to as 'dust') when the treated plant propagation material, such as a seed, is handled (improved dust-off). Further, such surface active compounds have also been found to provide compatibility between pesticidal compositions, especially where one has a lower pH.

Accordingly, in a first aspect, the present invention provides an aqueous seed treatment insecticidal and/or nematicidal composition in the form of a suspension comprising
(A) at least one insecticide and/or nematicide in an amount of at least 3 weight %, based on the total weight of the composition, and
(B) at least two surface active compounds, wherein (i) at least one is an anionic phosphate type compound, and (ii) at least one is a non-ionic alkoxylated phenol.

In an embodiment of the first aspect, a further pesticide is also present.

In a second aspect, the present invention provides a slurry composition (also referred to as "tank-mix" or "ready to apply") comprising the composition of the first aspect, a liquid carrier and optionally (i) one or more, preferably other, formulation adjuvants, (ii) one or more other pesticidal compositions, each comprising at least one further pesticide, or both (i) and (ii).

In a preferred embodiment of the second aspect, the slurry composition comprises the pesticidal composition of the first aspect, a liquid carrier, (i) one or more, preferably other, formulation adjuvants, and (ii) one or more other pesticidal compositions, each comprising at least one further pesticide.

In a third aspect, the present invention provides a method of protecting plant propagation material, preferably a seed, from attack by pests, such as soil-dwelling pests, preferably a nematode, by treating the material with a pesticidally, preferably a nematicidally, effective amount of the composition of the first or second aspect, preferably before planting or sowing the seed.

Accordingly, the invention also provides a method of controlling pests, such as a nematode, from damaging crop plants, especially selected from cotton, soybean and maize crop plants, by the treatment of the plants' propagation material, such as a seed, with a pesticidally, preferably a nematicidally, effective amount of the composition of the first or second aspect, preferably before planting or sowing the seed.

In a fourth aspect, the present invention provides a pest resistant plant propagation material comprising a plant propagation material, preferably a seed, such as a cotton, soybean or maize seed, treated with a pesticidally, preferably nematicidally, effective amount of the composition of the first or second aspect or obtained by the method of the third aspect.

In a fifth aspect, the present invention provides the use in a first or second aspect composition, to improve the dust-off property of a plant propagation material, preferably a seed, that has been treated with the composition, of at least two surface active compounds, wherein (i) at least one is an anionic phosphate type compound, and (ii) at least one is a non-ionic alkoxylated alcohol or phenol.

In another aspect, the present invention provides a method of improving the dust-off property of a plant propagation material, preferably a seed, that has been treated with a first or second aspect composition, said method comprising mixing in the pesticidal or slurry composition at least two surface active compounds, wherein (i) at least one is an anionic phosphate type compound, and (ii) at least one is a non-ionic alkoxylated alcohol or phenol In a sixth aspect, the present invention provides the use of at least two surface active compounds to improve the compatibility of a first pesticidal composition having a pH of 4 to less than 7, such as 4 to 6.5, preferably 4.5 to 6.5, more preferably 5 or 5.5 to 6.5, with a second pesticidal composition, wherein (i) at least one surface active compound is an anionic phosphate type compound, and (ii) at least one surface active compound is a non-ionic alkoxylated alcohol or phenol, and the surface active compounds are present either in (I) a slurry composition comprising the first and second pesticidal compositions, or (II) the second pesticidal composition.

In a further aspect, the invention also provides a method of improving the compatibility of a first pesticidal composition having a pH of 4 to less than 7 with a second pesticidal composition, said method comprising mixing, at least two surface active compounds, wherein (i) at least one is an anionic phosphate type compound, and (ii) at least one is a non-ionic alkoxylated alcohol or phenol, (I) in a slurry composition comprising the first and second pesticidal compositions, or (II) in the second pesticidal composition.

The invention is described in more detail below.

Compositions

It has now been found that higher concentrations of solids (e.g., active ingredients) are able to be incorporated and maintained in satisfactory compositions according to the present invention. Accordingly, in one embodiment, the pesticide (or active ingredient) is present in the composition of the first aspect in an amount of from about 12.5% to about 60% by weight, more specifically, from 30 to about 55%, such as 40 to 55%, by weight of the composition; the balance of the composition, also known as a formulation, comprising a water along with surfactant(s) and other optional inert ingredients known in the art as formulation adjuvants, e.g., protective colloids, adhesives, thickeners, thixotropic agents, penetrating agents, preservatives, stabilizers, antifoaming agents, antifreeze agents, sequestering agents, colourings, such as dyes or pigments, and polymers.

In the composition of the second aspect, the proportions of the components would be less than that in the first aspect and depends on the amount of the liquid carrier (typically water), which is normally present in a major proportion, and also on the presence of one or more, of the same or, other formulation adjuvants and/or one or more other pesticidal compositions each comprising a further pesticide.

The pesticide (or active ingredient) can be of any type, for example, a fungicide, such as triazole derivatives, strobilurins, carbamate (including thiocarbamate), benzimidazoles (thiabendazole), N-trihalomethylthio compounds (captan), substituted benzenes, carboxamides, phenylamides and phenylpyrroles, and mixtures thereof; an insecticide (such as neonicotinoids, carbamates and pyrethroids), acaricide, molluscicide and a nematicide. Preferably, the pesticide defined in the first aspect is an insecticide and/or nematicide.

Preferred examples of suitable active ingredients (whether insecticide, nematicide or fungicide) for a composition of the invention are selected from abamectin (1), acephate (2), acetamiprid (4), alpha-cypermethrin (202), azinphos-methyl (45), bifenthrin (76), carbaryl (115), carboxin (120), carbofuran (118), carbosulfan (119), chlorpyrifos (145), clothianidin (165), cyromazine (209), deltamethrin (223), dimethoate (262), emamectin benzoate (291), endosulfan (294), fipronil (354), furathiocarb (412), gamma-HCH (430), imidacloprid (458), Isofenphos, methiocarb (530), omethoate (594), tefluthrin (769), thiamethoxam (792), thiacloprid (791), thiodicarb (799), azoxystrobin (47), pyraclostrobin (690), benomyl (62), bitertanol (84), captan (114), carbendazim (116), carboxin (120), chlorothalonil (142), copper salts (such as copper sulfate (172), cuprous oxide (181), Bordeaux mixture (87), copper hydroxide (169), copper sulfate (tribasic) (173), copper oxychloride (171) and copper octanoate (170)), cymoxanil (200), cyproconazole (207), cyprodinil (208), difenoconazole (247), diniconazole (267), ethirimol, famoxadone (322), fenamidone (325), fenhexamid (334), fenpiclonil (341), fluazinam (363), fludioxonil (368), fluquinconazole (385), flutolanil (396), flutriafol (397), fosetyl-aluminium (407), fuberidazole (409), guazatine (422), hexaconazole (435), hymexazol (447), imazalil (449), iprodione (470), isofenphos, mancozeb (496), maneb (497), metalaxyl (516), metalaxyl-M (517), metconazole (525), myclobutanil (564), silthiofam (729), nuarimol (587), oxadixyl (601), oxine-copper (605), oxolinic acid (606), pencycuron (620), prochloraz (659), procymidone (660), pyrimethanil (705), pyroquilon (710), quintozene (716), tebuconazole (761), tetraconazole (778), thiabendazole (790), thiophanate-methyl (802), thiram (804), triadimenol (815), triazoxide (821), triticonazole (842), trifloxystrobin (832), picoxystrobin (647) and ipconazole (468).

In an embodiment of either the first or second aspect, the active ingredient is selected from the active ingredients abamectin (1), emamectin benzoate (291), metalaxyl-M (517), thiamethoxam (792), difenoconazole (247), azoxystrobin (47), tefluthrin (769), fludioxnil (368), imidacloprid (458), thiacloprid (791), clothianidin (165) and myclobutanil (564). Especially, the composition of the first aspect comprises abamectin, and advantageously, the composition of the second aspect comprises abamectin, a neonicotinoid (such as thiamethoxam), azoxystrobin, fludioxnil and metaixyl-M.

In a preferred embodiment, the pH of the composition of the first aspect and the second pesticidal composition of the sixth aspect is in the range of 6 to 8, such as 6.5 to 7.5 or 6 to 6.5.

The pesticides are described in the e-Pesticide Manual, version 3.0, 13th Edition, Ed. CDC Tomlin, British Crop Protection Council, 2003-04. The number following the compound name is the entry number given in the Pesticide Manual.

Generally compositions of the first aspect come in a suspension concentrate (SC) or flowable suspension (FS) concentrate form. Suspension concentrate formulations for seed treatment, generally have a viscosity of 300 to 1200, such as 400 to 800, $mPas^{-1}$, when measured in a BROOKFIELD viscometer with spindle 3 at 30 rpm and 25° C. The average size of the suspended particles is 0.1 to 20, especially 0.5 to 5, advantageously 1 to 3, microns, when measured with a laser particle analyzer, e.g., a Malvern Mastersizer S. Whereas, compositions of the second aspect tend to be a diluted version of the former.

The formulations, i.e., the compositions, preparations or combinations containing (A) and (B) components of the first aspect, are prepared in a known manner, for example, by intimately mixing and/or grinding the components with water.

The amount of surface active compounds (B) generally present range from 1 to 25, preferably 2.4 to 22.5, especially 5 to 10, %, by weight, based on the weight of the composition of the first aspect. Surface active compounds are made up of water soluble (hydrophilic) groups (or constituents), such as polyoxyethylene, and water insoluble (hydrophobic) groups (or constituents), such as polyoxypropylene. Examples of surface active compounds are surfactants having good emulsifying, dispersing and wetting properties, depending on the nature of the pesticide to be formulated. Surfactants will also be understood as meaning mixtures of surfactants.

In an embodiment, the molecular weight of the (B)(i) and (B)(ii) surface active compounds, independent of each other, is less than 2200, preferably less than 1700, such as in the range 400 to 1500, preferably in the range 600 to 1200.

The (B)(i) surface active compound preferably has a Hydrophile-Lipophilic Balance (HLB) of at least 10, preferably in the range 10 to 25, such as 12 to 20, preferably 14 to 18.

The (B)(ii) surface active compound preferably has a Hydrophile-Lipophilic Balance (HLB) of at least 5, preferably 7 to 20, such as 10 to 15.

In an embodiment, the weight ratio of surface active compounds (B)(i) to (B)(ii) is in the range of 1:10 to 10:1, preferably, 5:1 to 1:1, especially 3:1 to 1:1.

The Hydrophile-Lipophilic Balance (HLB) value is an index of the hydrophilic nature of a compound proposed by Griffin. The HLB value of a polyoxyethylene alkyl ether can be determined by, for example, the Griffin equation.

$$HLB \text{ value}=[(\text{molecular weight of the hydrophilic moiety})/(\text{molecular weight of the surface active compound})] \times 20$$

Groups, for example, sulfate and phosphate ions, can also contribute to the HLB value.

Generally, compounds, including surface active compounds, that are commercially used tend to be not analytically pure, but a mixture of suitable compounds, for example, of the same chemistry but of different analogs, isomers and molecular weights. The characteristics attributed to, for example, the (B)(i) and (B)(ii) surface active compounds are, therefore, preferably also satisfied in a mixture of compounds where the characteristics are possessed by a compound in the mixture, which compound is present in a major proportion, such as greater than 50, preferably greater than 60, especially greater than 75, % by weight, based on the weight of the mixture; more preferably, the mixture itself satisfies the characteristics defined.

The surfactants customarily employed in formulation technology are described, inter alia, in the following publications:
 "McCutcheon's Detergents and Emulsifiers Annual", MC Publishing Corp., Glen Rock, N.J., 1988.
 M. and J. Ash, "Encyclopedia of Surfactants", Vol. 1-Ill, Chemical Publishing Co., New York, 1980-1981.

Examples of a phosphate type surfactant include an alkylphenol polyalkoxyether phosphate, a block copolymer of polyalkoxyether phosphate, a polyarylphenol polyalkoxyether phosphate and an arylphenol polyalkoxyether phosphate.

Examples of alkoxylated alcohols include an alkoxylated alcohol (such as alkoxylated oil, alkoxlated alcohol having C5 to C18 carbon atoms in the alcohol).

Examples of alkoxylated phenols include alkylphenol polyalkoxyether and (poly)arylphenol polyalkoxyether.

Preferably, the (B)(ii) compound is an alkoxylated phenol. The anionic surfactants may be present as acids or include alkali metals (such as lithium, sodium and potassium), alkali earth metals (such as calcium and magnesium), ammonium and various amines (such as alkylamines, cycloalkylamines and alkanolamines).

Specific examples of suitable anionic surfactants include: Soprophor 3D33 (Rhodia), Sorprophor PS19 (Rhodia) and Dowafax 30 C05 (Dow).

Specific examples of non-ionic surfactants include: Synperonic NP (Uniqema), Soprophor BSU (Rhodia), Rhodasurf BC-610 (Rhodia), Toximul 8240 (Stepan) and Synperonic 91/4 (Uniqema).

The compositions of the invention can also contain a wetting agent, which is also considered surface active compound in that it has a water soluble (hydrophilic) and water insoluble (hydrophobic) components, but they tend to non-ionic and generally have a molecular weight of less than 2000, and so can be a component according to (B)(ii). In a preferred embodiment of the first aspect, a wedding agent is not present.

Advantageously, two surface active compounds, one of (B)(i) and one of (B)(ii), are used in the compositions according to the first aspect.

The compositions of the invention also may comprise at least one antifreeze agent. In an embodiment, the antifreeze agent is present in at least about 2 and up to about 25% of, more specifically from 3 to about 10% by weight, based on the weight of the composition of the first aspect.

Specific examples of suitable antifreezes include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, and octaglycerol.

As a particularly preferred subset of suitable antifreeze materials there can be mentioned ethylene glycol, propylene glycol and glycerol.

The compositions of the invention optionally includes at least one polymer selected from water-soluble and water-dispersible film-forming polymers. Suitable polymers have an average molecular weight of at least about 7,000 up to about 200,000; more specifically at least about 10,000, up to about 100,000. The compositions of the invention generally contain from about 0% to about 10% by weight of the composition of polymer, preferably in an amount of from 1 to 7, such as 2 to 6, % by weight, based on the weight of the composition of the first aspect. As used herein, "nonionic surfactants" are different compounds from the water-dispersible and water-soluble polymers described herein.

Suitable polymers are selected from
d1) ethylene vinylacetate copolymers,
d2) vinylacetate/vinylpyrrolidone copolymers,
d3) alkylated vinylpyrrolidone copolymers,
d4) polyvinylpyrrolidone, and
d5) polyalkyleneglycol including the polypropylene glycols and polyethylene glycols.

The compositions of the invention also optionally contains at least one thickener. In one embodiment, the thickener is present in an amount from about 0.01% to about 5% w/w, more specifically from 0.05 to 2% by weight, based on the weight of the composition of the first aspect.

Illustrative of thickeners (water-soluble polymers which exhibit pseudoplastic properties in an aqueous medium) are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of the maleic anhydride copolymers, and alkali metal salts of poly(meth)acrylate.

As suitable thickeners there may also be mentioned attapulgite-type clay, carrageenan, croscarmellose sodium, furcelleran, glycerol, hydroxypropyl methylcellulose, polystyrene, hydroxypropyl cellulose, hydroxypropyl guar gum, and sodium carboxymethylcellulose. Xanthan gum and attapulgite-type clay are preferred.

The compositions of the invention can be employed together with the adjuvants customary in formulation technology, biocides, biostats, emulsifiers (lethicin, sorbitan, and the like), antifoam agents or application-promoting adjuvants customarily employed in the art of formulation. In addition, there may be mentioned inoculants and brighteners.

Additionally, a colouring agent, such as a dye or pigment, is included in the seed coating so that an observer can immediately determine that the seeds are treated. The colouring agent is also useful to indicate to the user the degree of uniformity of the coating applied. Generally, the colouring agent is also suspended in the compositions of the present invention.

The compositions of the invention can be prepared by processes known in the art, such as forming a homogeneous suspension with all the components, except the thickeners, and wet milling the suspension until the desired particle size is reached, then the thickeners and further water are added to a set viscosity.

The final composition can be screened if desired to remove any insoluble particles.

In one embodiment, commercial products according to the first aspect will preferably be formulated as concentrates (also known as "formulated products" or "pre-mix"). They may be used undiluted or may be diluted with a liquid carrier, such as water, and one or more components in a tank before using. The decision to dilute (by adding other components or liquid carrier) depends on the treatment methods available to the user. The composition according to the second aspect (also known as a "tank mix" or "ready to apply") is an example of diluting the composition of the first aspect. The liquid carrier in the slurry composition tends to be water, The composition according to the first aspect may contain or be applied sequentially with further compounds on to the propagation material, such as a seed, to form a seed dressing. These further compounds can be fertilizers or micronutrient donors or other preparations that influence plant growth. They can also be selective herbicides, fungicides, other insecticides, bactericides, insect growth regulators, plant growth regulators, nematicides, molluscicides or mixtures of several of these preparations.

The pesticidal composition of the first aspect may be used alone or in combination with other pesticidal compositions for treatment of propagation material either together or sequentially. In a preferred embodiment, a composition of the first aspect is used in a slurry with other pesticidal compositions to treat seeds.

Generally, a composition of the second aspect is that applied for controlling pests, such as by treating propagation material. In such an event, such a composition would contain more types of formulation components than a composition of the first aspect, which is an ingredient in the preparation of the composition of the second aspect.

Uses

The compositions of the present invention can be used to control pests from plants by conventional methods.

The pesticidal compositions according to first and second aspects are used for the treatment of plant propagation material so that material has a degree of protection during its germination and growth.

The term "plant propagation material" is understood to denote all the generative parts of the plant, such as seeds, which can be used for the multiplication of the latter and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

The pesticidal compositions according to first and second aspects are especially suited to treatment of seeds. The techniques of seed treatment application are well known to those skilled in the art, and they may be used readily in the context of the present invention. For the purposes of this invention, seed treatments are defined as chemical or biological substances that are applied to seeds or vegetative plant propagation materials to control disease organisms, insects, or other pests. The seed treatment composition includes the pesticides, such as fungicides, bactericides, nematicides and other classes of insecticides. Most seed treatments are applied to true seeds, which have a seed coat surrounding an embryo. However, some seed treatments can be applied to vegetative plant propagation materials such as rhizomes, bulbs, corms or tubers.

The composition of the first aspect may be used, for example, for treatment, in an undiluted form or be diluted with a liquid carrier, for example. In the instance it is diluted, such compositions are known as slurries or tank mix and represent an example of the second aspect of the invention. The compositions of the first and second aspect may be applied to a seed to result in a film (or dressing), a coating, or a pellet, of the pesticide on the seed after drying, depending on the treatment process. The processes are well known in the art, and employ, for seeds, e.g., the techniques of film-coating or encapsulation, or for the other propagation material, the techniques of, e.g., immersion. Needless to say, the method of application of the compounds to the seed may be varied and the invention is intended to include any technique which is to be used.

The compositions of the invention are formulated for protecting cultivated plants and their propagation materials. The compositions are advantageously formulated for seed treatment applications against soil inhabiting insects, which can damage the crop in the early stages of plant development. For example, the compositions can be formulated to target insects and representatives of the order Acarnia including:

from the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Coleoptera, for example,

*Agriotes* spp., *Anthonomus* spp., Atomaria linearis, *Chaetocnema* tibialis, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp.;

from the order Orthoptera, for example,

*Blatta* spp., *Blattella* spp., *Gryllotalpa* spp., *Leucophaea maderae*, *Locusta* spp., *Periplaneta* spp. and *Schistocerca* spp.;

from the order Isoptera, for example,

*Reticulitermes* spp.;

from the order Psocoptera, for example,

*Liposcelis* spp.;

from the order Anoplura, for example,

Haematopinus spp., Linognathus spp., Pediculus spp., Pemphigus spp. and Phylloxera spp.;

from the order Mallophaga, for example,

Damalinea spp. and Trichodectes spp.;

from the order Thysanoptera, for example, Frankliniella spp., Hercinothrips spp., Taeniothrips spp., Thrips palmi, Thrips tabaci and Scirtothrips aurantii;

from the order Heteroptera, for example,

Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp. and Triatoma spp.;

from the order Homoptera, for example, Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;

from the order Hymenoptera, for example,

Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.;

from the order Diptera, for example,

Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp. and Tipula spp.;

from the order Siphonaptera, for example, Ceratophyllus spp. und Xenopsylla cheopis and from the order Thysanura, for example, Lepisma saccharina;

crucifer flea beetles (Phyllotreta spp.), root maggots (Delia spp.), cabbage seedpod weevil (Ceutorhynchus spp.) and aphids; and from the order Acarina, for example, Acarus siro, Aceria sheldoni, Aculus schlechtendali, Amblyomma spp., Argas spp., Boophilus spp., Brevipalpus spp., Bryobia praetiosa, Calipitrimerus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp. and Tetranychus spp.

Protection of developing plants against attack by plant parasitic nematodes is also obtainable in the instance the pesticide is, for example, Abamectin. Abamectin is effective against a wide range of nematode pests including species of Meloidogyne (for example, Meloidogyne incoginita and Meloidogyne javanica), Heterodera (for example, Heterodera glycines, Heterodera schachtii, Heterodera avenae and Heterodora trifolii), Globodera (for example, Globodera rostochiensis), Radopholus (for example, Radopholus similes), Rotylenchulus, Pratylenchus (for example, Pratylenchus neglectans and Pratylenchus penetrans), Aphelenchoides, Helicotylenchus, Hoplolaimus, Paratrichodorus and Tylenchorhynchus, in particular Meloidogyne.

The composition of the first and second aspect, in the case abamectin is present as a pesticide, are particularly effective in controlling nematodes.

Optionally, in addition to the control of insect pests, the compositions of the invention advantageously are formulated with fungicides for seed treatment applications against diseases in the soil, which mostly occur in the early stages of plant development. For example, the compositions can be formulated to target pathogens including Pythium, Tilletia, Gerlachia, Septoria, Ustilago, Fusarium, Rhizoctonia (so-called "damping off complex"); Oomycetes such as Phytophthora, Plasmopara, Pseudoperonospora, Bremia etc. as well as against the Botrytis species, Pyrenophora, Monilinia and further representatives of the Ascomycetes, Deuteromycetes and Basidiomycetes classes.

Suitable target crops are especially potatoes, cereals, (wheat, barley, rye, oats), rice, maize, sugar beet, cotton, millet varieties, sorghum, tobacco, sun flowers, beans, peas, oil plants (rape, canola), soybeans, cabbages, tomatoes, eggplants (aubergines), pepper and other vegetables, and spices as well as ornamental shrubs and flowers.

Suitable target crops also include transgenic crop plants of the foregoing varieties. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from Bacillus thuringiensis strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The compositions are suited for dressing applications on plant propagation material. The latter term embraces seeds of all kinds (fruit, tubers, grains), cuttings, cut shoots and the like. The preferred field of application is the treatment of all kinds of seeds (as specified in the target crops above), and in particular the seed treatment of canola, maize, cereals, cotton, tomatoes, tobacco, soybeans, other legumes, and other vegetables and crops that are susceptible, especially preferred are cotton, maize and soybean crop seeds.

As noted above, the compositions of this invention may be formulated or mixed in the seed treater tank or combined on the seed by overcoating with other pelleting materials and/or seed treating agents. The agents to be mixed with the compounds of this invention may be for the control of pests, nutrition, and the control of plant diseases.

The composition has particular application to concurrent and sequential seed treatments. Seeds treated with the compositions of the invention generally have a drying time ranging from 20 to 60 seconds when being treated at room temperature. Generally, for vegetable seeds a spray drying technique is used.

A preferred method of applying the composition according to the invention consists in spraying or wetting the plant propagation material with the liquid preparation, or mixing the plant material with such liquid preparation. Also, before the application, the composition of the invention may be diluted with water by simple mixing at ambient temperature in order to prepare an on-farm seed treatment formulation.

The formulation may be applied, for low value crops, such as cereals, at application volumes ranging from 200 ml to 3 liters per 100 kg seed, more specifically, from 400 ml to 2 liters per 100 kg seed. For vegetable crop seeds, the amount tend to be higher.

A beneficial feature of the composition is that it provides an increased adherence of particles, in particular air-borne particles, to the seed, which results in decreased dustiness and the subsequent elimination of related dust problems. Elimination of the dust associated with many seed treatments also eliminates the associated health hazards to those who work with treated seeds, such as processing plant employees, truck drivers, warehouse workers, and farmers. The compositions of the present invention also enable satisfactory flowability & individuality of the propagation material (i.e., allow the material to be easily handled and not stick to each other).

Still another advantage of this invention is the uniform coating of seeds with non-dusting seed treatment which will not interfere with germination and sprouting of the seed but which will protect the seed and resultant seedling against pests, particularly soil-borne pests.

The application of a the compositions according to the invention directly on a seed, seed piece or bare root dip treatment for early season crop protection has several distinct advantages both from an economic and environmental standpoint. By treating seeds, seed pieces or bare roots, preferably prior to planting or sowing, with a pesticide, for example, a nematicide in the case of Abamectin, the pesticide is concentrated at the site of pest, e.g., nematode, attack and, therefore, much less active ingredient on a per acre basis is required in comparison with conventional soil application. This not only makes pest control more economic, but also minimizes environmental disturbance and any adverse non-target effects.

As used in the present application, the embodiments of the features of the present invention are independent of each other, unless otherwise specified.

The following Examples are given by way of illustration and not by way of limitation of the invention.

EXAMPLES

Formulation examples A, B, 1 and 2 are prepared by mixing surfactant(s), thickening agent, polymer (if any), suspension aid (if any), a defoaming agent, a preservative and an antifreeze agent, with water until a homogeneous phase is achieved. Subsequently, abamectin is added and is mixed. The resulting mixture is then wet-milled through a so-called bead mill (Dyno, Drais, Premier for instance). The milling parameters are set in such a way that the average particle size of the resulting ground premix is within specifications (usually median particle size average at most 2.0 um). Finally, the buffer (if any) and a minor amount of water are added and the final product is mixed for at least 30 minutes. Table 1 indicates their compositional details, with the antifoam, preservative, thickening agent and water omitted.

Compatibility Studies

Each pesticidal formulation example A, B, 1 and 2 is mixed with an insecticide formulation (X) having a about pH of 5.5 to form a slurry composition and its compatibility is observed. It is found that examples 1 and 2 provided better compatibility (i.e., less flocculation and better homogeneity) than examples A and B.

Seed Treatment Studies

The treat-rate of the compositions on to the seeds is such that equivalent amount of solid material (e.g., active ingredient and colour agent) is applied on to the seeds.

No Abamectin Composition:

A slurry composition containing a insecticide formulation (X), a composition (Y) containing calcium carbonate, a fungicide pesticidal formulation and a colour agent, a polymer (Z) and water is treated by Hege seed treatment device onto cotton seeds.

No Polymer:

Each pesticidal formulation example A, B, 1 and 2 is mixed with an insecticide formulation (X) and water, and is treated by Hege seed treatment device onto cotton seeds that have already been treated with a composition (Y) containing calcium carbonate, a fungicide pesticidal formulation and a colour agent.

Dust-off Measurements

The amount of 'dust' given off by the treated seeds is measured by placing the treated seeds in a plastic drum with ridges, which when the drum is rotated stimulates handling and conveying of the seeds. A precision airflow control system provides a constant flow of air that carries air borne particles through a coarse filter separator onto a filter. The dust quantity is measured by weighing the filter. The data from the 'dust-off' measurements is given in Table 2.

The data clearly show that seeds treated with compositions containing the combination surface active compounds (formulations 1 and 2) provide less air-borne particles, i.e., better dust-off, compared to compositions containing formulations A and B. Furthermore and surprisingly, the amount of dust from compositions containing formulations 1 and 2 is less than that of the seeds treated with a composition no containing Abamectin, i.e., a composition with less solids content on the seed.

TABLE 1

| | Mass % | | | |
|---|---|---|---|---|
| | A | B | 1 | 2 |
| abamectin | 46.30 | 46.30 | 46.30 | 46.30 |
| non-ionic alkoxylated phenol (surfactant) | — | — | 1.0 | 1.0 |
| anionic phosphate type (surfactant) | — | — | 1.5 | 1.5 |
| EO-PO block copolymer (surfactant) | 2.5 | 2.5 | — | — |
| Polyvinylpyrrolidone (polymer) | 0.1 | 0.1 | — | — |
| Silicic acid (suspension aid) | 1.0 | 1.0 | — | — |
| pH buffer | 0.77 | 0.77 | | — |
| Antifreeze 1 | — | 5.0 | 5.0 | — |
| Antifreeze 2 | 5.0 | — | — | 5.0 |

TABLE 2

| | | no polymer | | | |
|---|---|---|---|---|---|
| | no abamectin | A | B | 1 | 2 |
| average milligrams of dust per 50 grams of cotton seeds | 5.9 | 10.4 | 7.5 | 5.1 | 5.1 |

The invention claimed is:

1. An aqueous seed treatment composition in the form of a suspension comprising (A) abamectin in an amount from about 30 weight % to about 60 weight %, based on the total weight of the composition, and (B) at least two surface active compounds in an amount from about 1 weight % to about 10 weight %, based on the total weight of the composition, wherein (i) at least one is alkylphenol polyalkoxyether phosphate, a block copolymer of polyalkoxyether phosphate, a polyarylphenol polyalkoxyether phosphate, an arylphenol polyalkoxyether phosphate, or mixtures thereof, and (ii) at least one is a non-ionic alkoxylated phenol.

2. The composition according to claim 1 wherein the molecular weight of the (B)(i) surface active compound is less than 2200.

3. The composition according to claim 1 wherein the molecular weight of the (B)(ii) surface active compound is less than 2200.

4. A slurry composition comprising the composition defined in claim 1, a liquid carrier and optionally (i) one or more formulation adjuvants, (ii) one or more other pesticidal compositions, each comprising at least one further pesticide, or both (i) and (ii).

5. The slurry composition according to claim 4 wherein one or more pesticidal compositions (ii) has a pH of less than 7.

6. A pest resistant plant propagation material comprising a plant propagation material treated with a pesticidally effective amount of the composition claimed in claim 1 to protect the plant propagation material from soil-dwelling pests.

7. An aqueous seed composition in the form of a suspension comprising an effective amount of the composition claimed in claim 1, wherein the molecular weight of B(i) is in the range 600 to 1200, and the molecular weight of B(ii) is in the range 600 to 1200, and (A) comprises abamectin.

8. A pest resistant plant propagation material comprising a plant propagation material treated with a pesticidally effective amount of the composition claimed in claim 7 to protect the plant propagation material from soil-dwelling pests.

9. A method of protecting plant propagation material from attack by soil-dwelling pests comprising treating the material with a pesticidally effective amount of the composition claimed in claim 1.

10. A method of protecting plant propagation material from attack by soil-dwelling pests comprising treating the material with a pesticidally effective amount of the composition claimed in claim 1, wherein the molecular weight of B(i) is in the range 600 to 1200, and the molecular weight of B(ii) is in the range 600 to 1200.

* * * * *